(12) United States Patent
Nakano

(10) Patent No.: US 8,708,890 B2
(45) Date of Patent: Apr. 29, 2014

(54) ENDOSCOPE APPARATUS AND METHOD OF MEASURING SUBJECT

(75) Inventor: Sumito Nakano, Tokyo (JP)

(73) Assignee: Olympus Corporation, Tokyo (JP)

( * ) Notice: Subject to any disclaimer, the term of this patent is extended or adjusted under 35 U.S.C. 154(b) by 595 days.

(21) Appl. No.: 12/911,933

(22) Filed: Oct. 26, 2010

(65) Prior Publication Data

US 2011/0178371 A1    Jul. 21, 2011

(30) Foreign Application Priority Data

Jan. 15, 2010    (JP) ................ P2010-006941

(51) Int. Cl.
*A61B 1/04* (2006.01)
*H04N 13/04* (2006.01)

(52) U.S. Cl.
USPC ............................................. 600/111; 348/51

(58) Field of Classification Search
USPC .................. 600/111, 114, 117, 166; 382/128; 345/157; 715/863; 348/51
See application file for complete search history.

(56) References Cited

U.S. PATENT DOCUMENTS

| | | | |
|---|---|---|---|
| 4,935,810 A | 6/1990 | Nonami et al. | |
| 5,655,033 A | 8/1997 | Inoguchi et al. | |
| 6,063,023 A | 5/2000 | Sakiyama et al. | |
| 2006/0176321 A1* | 8/2006 | Nakano et al. | 345/660 |
| 2006/0268257 A1 | 11/2006 | Ogawa | |
| 2007/0165306 A1 | 7/2007 | Bendall et al. | |
| 2008/0240491 A1* | 10/2008 | Hori | 382/100 |
| 2009/0167847 A1 | 7/2009 | Doi | |

FOREIGN PATENT DOCUMENTS

| | | |
|---|---|---|
| JP | 04-166708 A | 6/1992 |
| JP | 06-180218 A | 6/1994 |
| JP | 2006-180218 A | 6/1994 |
| JP | 06-243258 A | 9/1994 |
| JP | 11-094527 A | 4/1999 |
| JP | 2001-195596 A | 7/2001 |
| JP | 2001-266128 A | 9/2001 |
| JP | 2005-251122 A | 9/2005 |
| JP | 2005-348870 A | 12/2005 |
| JP | 2006-145419 A | 6/2006 |
| JP | 2006-325741 A | 12/2006 |
| JP | 2006-329684 A | 12/2006 |
| JP | 2008-185895 A | 8/2008 |
| JP | 2009-086552 A | 4/2009 |
| JP | 2009-086553 A | 4/2009 |
| JP | 2009-258273 A | 11/2009 |
| WO | WO 2007/072102 A1 | 6/2007 |

* cited by examiner

*Primary Examiner* — Anhtuan T Nguyen
*Assistant Examiner* — Alexandra Newton
(74) *Attorney, Agent, or Firm* — Holtz, Holtz, Goodman & Chick, PC

(57) ABSTRACT

An endoscope apparatus includes: a display device that displays a first image and a second image, the first image and the second image being contained in image data of a subject captured by an imaging unit of an endoscope apparatus; a designation section that designates a first position on the first image in accordance with an instruction input through an input device; a position calculation section that calculates a second position on the second image, the second position corresponding to the first position on the first image; a display control section that, when the first position is designated, performs a control of displaying a mark at the first position, subsequently displaying a mark at a third position which is different from the first and second positions, and subsequently displaying a mark at the second position; and a measurement section that performs measurement relating to the subject based on the first and second positions.

12 Claims, 18 Drawing Sheets

89c 89c  89d

ENDOSCOPE APPARATUS AND METHOD OF MEASURING SUBJECT

BACKGROUND OF THE INVENTION

1. Field of the Invention

The present invention relates to an endoscope apparatus which images a subject. The present invention also relates to a method of measuring a subject.

Priority is claimed on Japanese Patent Application No. 2010-006941, filed Jan. 15, 2010, the content of which is incorporated herein by reference.

2. Description of Related Art

Industrial endoscope apparatuses are used to observe or inspect inside damage, corrosion, and the like of a boiler, a turbine, an engine, a pipe, and the like. Moreover, there is an endoscope apparatus having a function of measuring the length, area, and the like using the principle of triangulation based on a measurement point designated on an image imaged by the endoscope. This endoscope apparatus has a plurality of kinds of optical adapters prepared to observe and inspect various objects, and a distal portion of the endoscope apparatus can be replaced.

An example of such an optical adapter includes a stereo optical adapter capable of imaging two subject images relating to the same subject. Using the stereo optical adapter, the length, area, and the like of the subject can be measured by calculating three-dimensional spatial coordinates of the subject using the principle of triangulation based on the coordinates of left and right optical system distance calculating points when the subject images are captured by the left and right optical systems.

FIGS. 20A and 20B show an example of a screen (hereinafter, referred to as measurement screen) which is displayed by a display device of an endoscope apparatus at the time of the measurement mode. A left image 900a and a right image 900b corresponding to left and right subject images captured by a stereo optical adapter are displayed on the measurement screen shown in FIG. 20A.

A cursor 910 for designating a measurement point indicating a measurement position is displayed on the left image 900a. A corresponding point cursor 920, which indicates a position of a corresponding point corresponding to the position of the cursor 910, is displayed on the right image 900b. The display position of the cursor 910 is set based on the instruction that the user inputs to the endoscope apparatus. When the cursor 910 is set in the left image 900a, matching processing is performed to calculate a position, on the right image 900b, of a corresponding point corresponding to the display position of the cursor 910.

The user can move the cursor 910 within the display screen by inputting the movement instruction of the cursor 910 to the endoscope apparatus. The corresponding point cursor 920 is moved along with the movement of the cursor 910. As shown in FIG. 20B, when the user inputs an instruction of designating (fixing) a measurement point after moving the cursor 910 to a desired position, a measurement point mark 930 indicating the position of the designated measurement point is displayed at the position of the cursor 910, and a corresponding point mark 940 is displayed at the position of the corresponding point corresponding to the measurement point. After a plurality of measurement points are designated, the measurement of the subject is performed based on the positions of the measurement points. Details of a measurement procedure of a subject based on a plurality of measurement points on a left image and their corresponding points on a right image is disclosed, for example, in Japanese Unexamined Patent Application, First Publication No. 2008-185895.

SUMMARY OF THE INVENTION

An endoscope apparatus according to an aspect of the invention includes: a display device that displays a first image and a second image, the first image and the second image being contained in image data of a subject captured by an imaging unit of an endoscope apparatus; a designation section that designates a first position on the first image in accordance with an instruction input through an input device; a position calculation section that calculates a second position on the second image, the second position corresponding to the first position on the first image; a display control section that, when the first position is designated, performs a control of displaying a mark at the first position, subsequently displaying a mark at a third position which is different from the first and second positions, and subsequently displaying a mark at the second position; and a measurement section that performs measurement relating to the subject based on the first and second positions.

DETAILED DESCRIPTION OF THE INVENTION

Figure 1:
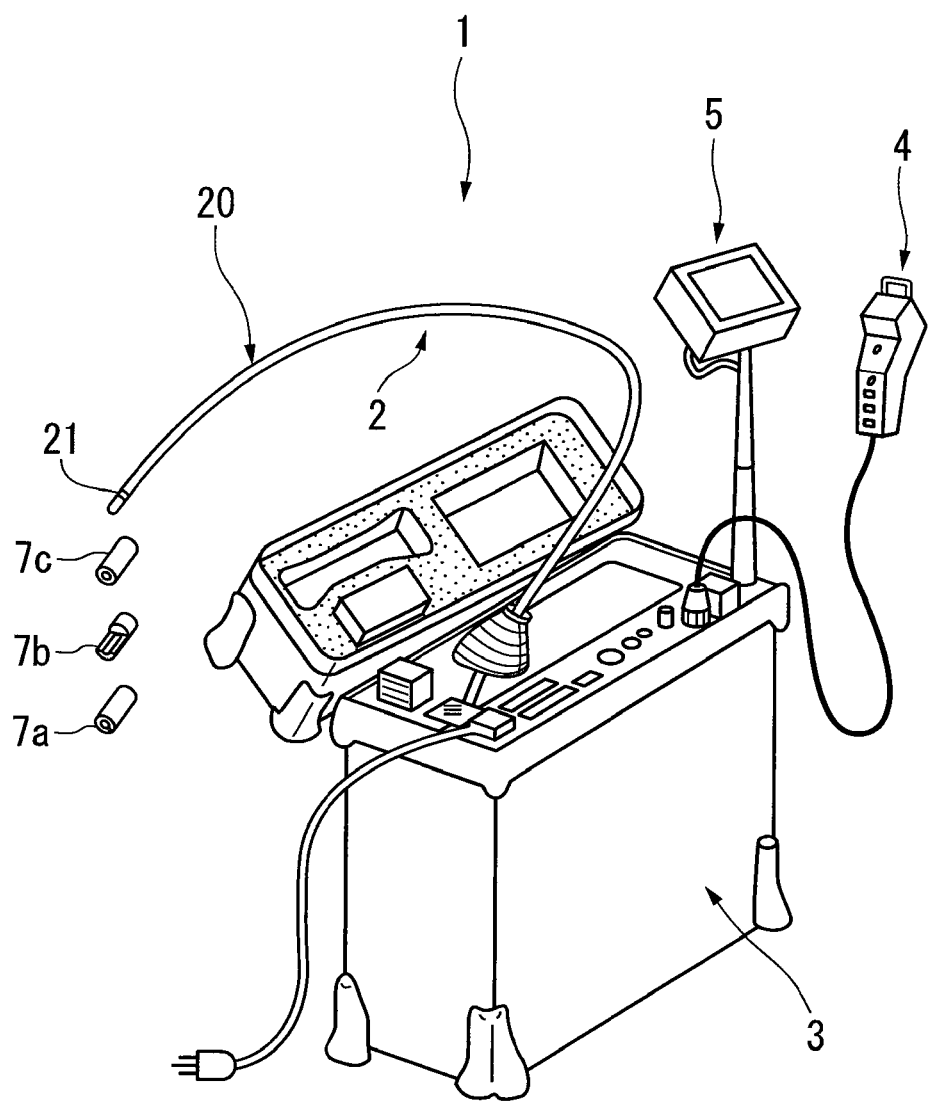
FIG. 1 is a perspective view illustrating the entire configuration of an endoscope apparatus according to an embodiment of the present invention.

Hereinafter, embodiments of the present invention will be described with reference to the drawings. FIG. 1 shows the configuration of an endoscope apparatus according to an embodiment of the present invention. As shown in FIG. 1, an endoscope apparatus 1 includes: an endoscope 2 having a long and thin insertion portion 20; a main unit 3; a remote controller 4 for performing an operation required for executing various kinds of operation controls of the entire apparatus; and an LCD 5 (liquid crystal display) as a display device. The main unit 3 has a housing in which the insertion portion 20 of the endoscope 2 is housed. The LCD 5 displays an endoscope image, the contents of an operation control (for example, a processing menu), and the like.

The insertion portion 20 includes a hard distal portion 21 and a flexible tube portion with the flexibility (for example, a bent portion 22 capable of being bent, for example, in the vertical and horizontal directions (FIG. 2)). Various kinds of optical adapters, such as a stereo optical adapter 7a or 7b having two observation fields of view or a normal observation optical adapter 7c having one observation field of view, can be attached to the distal portion 21 in a freely detachably manner.

Figure 2:
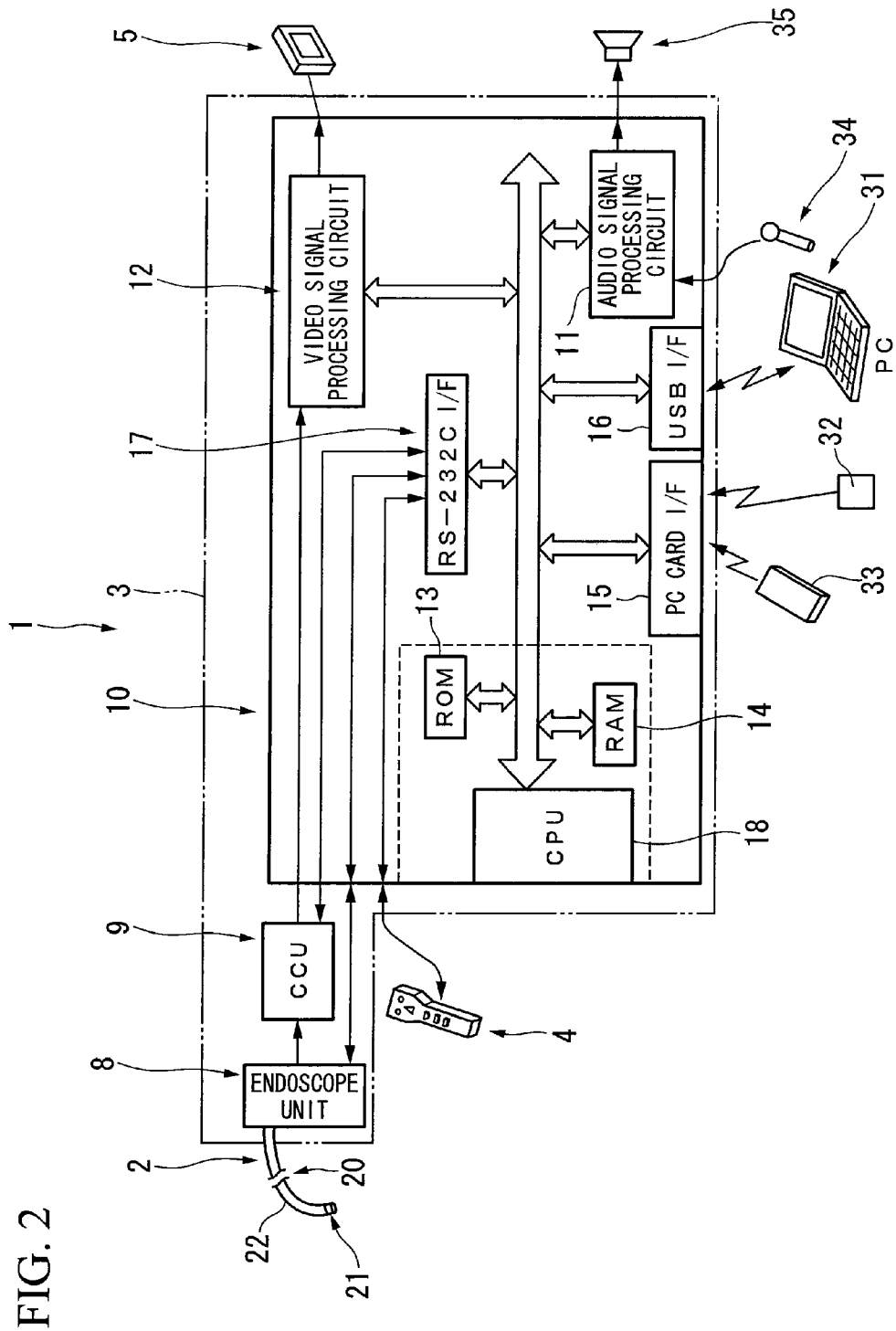
FIG. 2 is a block diagram illustrating the internal configuration of the endoscope apparatus according to the embodiment of the present invention.

As shown in FIG. 2, an endoscope unit 8, a CCU 9 (camera control unit), and a control unit 10 are provided in the main unit 3. A proximal portion of the insertion portion 20 is connected to the endoscope unit 8. The endoscope unit 8 includes a light source (not shown) for supplying necessary illumination light at the time of observation, and a bending device (not shown) for bending the bent portion 22 constituting the insertion portion 20.

A solid-state imaging device 2a (refer to FIG. 6) is built in the distal portion 21 of the insertion portion 20. The solid-state imaging device 2a generates an image signal by performing photoelectric conversion on a subject image formed through the optical adapter. The image signal output from the solid-state imaging device 2a is input to the CCU 9. The image signal is converted into a video signal, such as an NTSC signal, in the CCU 9 and is then supplied to the control unit 10.

An audio signal processing circuit 11, a video signal processing circuit 12 to which the video signal is input, a ROM 13, a RAM 14, a PC card I/F 15 (PC card interface), a USB I/F 16 (USB interface), an RS-232C I/F 17 (RS-232C interface), and a CPU 18 that executes these various functions based on a main program and that performs various controls are provided in the control unit 10.

The CCU 9 and the endoscope unit 8 are connected to the RS-232C I/F 17. In addition, the remote controller 4 which performs control and operation instructions of the CCU 9, endoscope unit 8, and the like is connected to the RS-232C I/F 17. When a user operates the remote controller 4, a communication required for controlling the CCU 9 and the endoscope unit 8 is performed based on the operation.

The USB I/F 16 is an interface for electrically connecting the main unit 3 and a personal computer 31 to each other. By connecting the main unit 3 to the personal computer 31 through the USB I/F 16, various kinds of instruction and controls, such as an instruction to display an endoscope image and image processing at the time of measurement, can be performed at the side of the personal computer 31 as an endoscope system. In addition, input and output of various kinds of control information or data, which is required for various processing, between the main unit 3 and the personal computer 31 can be performed.

A so-called memory card, which is storage medium such as a PCMCIA memory card 32 or a flash memory card 33, can be freely attached to or detached from the PC card I/F 15. By mounting the memory card in the card I/F 15, it is possible to take data, such as control processing information or image information, stored in the memory card into the main unit 3, or to store data, such as the control processing information or the image information, in the memory card, in accordance with the control of the CPU 18.

In order to display a synthesized image obtained by synthesizing the endoscope image supplied from the CCU 9 with a graphic image of operation menu and various GUI components (a cursor and the like), the video signal processing circuit 12 performs processing for synthesizing a graphic image signal based on the operation menu and the various GUI components, which is generated by the control of the CPU 18, with the video signal from the CCU 9, processing required for displaying the synthesized image on the screen of the LCD 5, and the like, and supplies the video signal to the LCD 5. In addition, the video signal processing circuit 12 may also perform processing for simply displaying an endoscope image or an operation menu image, independently. Accordingly, the endoscope image, the graphic image of operation menu, and the like, or the synthesized image obtained by synthesizing the endoscope image with the graphic image of operation menu, and the like, is displayed on the screen of the LCD 5.

The video signal processing circuit 12 outputs image data, which is based on the video signal from the CCU 9, to the CPU 18. At the time of measurement, since a stereo optical adapter is attached to the distal portion 21, a plurality of subject images relating to the same subject as a measurement target are included in an image based on the image data from the video signal processing circuit 12. In the present embodiment, a pair of left and right subject images is included, by way of example.

An audio signal generated by collecting sound with a microphone 34 and stored in storage medium such as a memory card, an audio signal obtained by playing storage medium such as a memory card, or an audio signal generated by the CPU 18 is supplied to the audio signal processing circuit 11. The audio signal processing circuit 11 performs processing, such as amplification processing, required for playing the supplied audio signal on the audio signal, and outputs it to a speaker 35. Thereby, an audio is output from the speaker 35.

The CPU 18 controls the entire system by executing a program stored in the ROM 13 in order to control various circuit portions to perform desired processing. At the time of measurement, the CPU 18 takes in the image data from the video signal processing circuit 12 and executes measurement processing based on the image data. The CPU 18 uses the RAM 14 as a working area for temporarily storing data.

Figure 3:
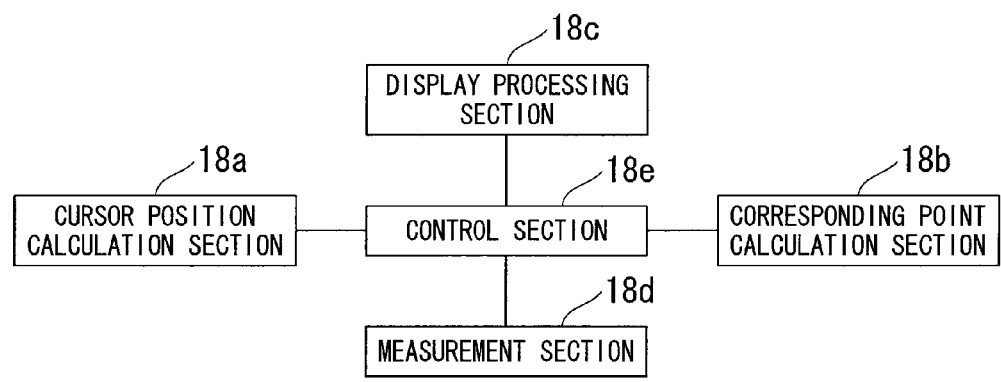
FIG. 3 is a block diagram illustrating the functional configuration of a CPU provided in the endoscope apparatus according to the embodiment of the present invention.

FIG. 3 shows a functional configuration of a part of the CPU 18 which is mainly described in the present embodiment. The CPU 18 includes a cursor position calculation section 18a, a corresponding point calculation section 18b, a display processing section 18c, a measurement section 18d, and a control section 18e.

The cursor position calculation section 18a detects a movement instruction of a cursor based on a signal from the remote controller 4 as an input device used by the user, and calculates a position of the cursor after movement on a left image. This position becomes a position of a measurement point. When the user inputs an instruction of designating (fixing) a measurement point through the remote controller 4, the cursor position calculation section 18a designates (recognizes) the calculated position of the cursor as a position of a measurement point of the measurement target.

The corresponding point calculation section 18b performs matching processing to calculate a position, on a right image, of a corresponding point corresponding to the position, on the left image, of the cursor designated by the cursor position calculation section 18a using image pattern matching. The display processing section 18c generates a graphic image signal of a cursor, a measurement point mark, a corresponding point mark, and the like, which are displayed so as to be superimposed on the images of the subject, and outputs it to the video signal processing circuit 12. Further, the display processing section 18c controls the display position of the cursor, the measurement point mark, the corresponding point mark, and the like on the image displayed on the LCD 5.

The measurement section 18d executes various measurements (for example, object distance measurement, point-to-point distance measurement, and area measurement) relating the subject based on the image data acquired from the video signal processing circuit 12. The control portion 18e controls the cursor position calculation section 18a, the corresponding point calculation section 18b, the display processing section 18c, and the measurement section 18d, and controls the overall operation of the endoscope apparatus 1.

Figure 4:
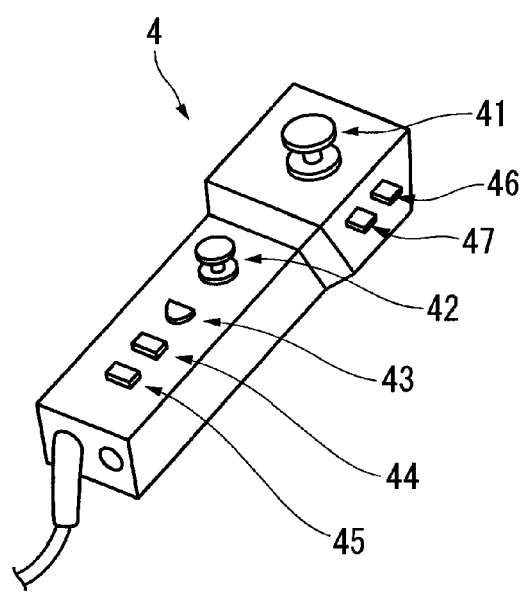
FIG. 4 is a perspective view of a remote controller provided in the endoscope apparatus according to the embodiment of the present invention.

As shown in FIG. 4, a joystick 41, a lever switch 42, a freeze switch 43, a store switch 44, and a measurement execution switch 45 are provided on the front surface of the remote controller 4. A WIDE switch 46 and a TELE switch 47 are provided on the side surface of the remote controller 4.

The joystick 41 is a switch that is operated for specifying a bending operation of the bent portion 22. When the user tilts the joystick 41, the bent portion 22 is bent in a direction corresponding to the tilt direction by an amount corresponding to the tilt angle. In addition, it is possible to input a fine adjustment instruction of the bending operation by pushing the joystick 41 directly downward. The lever switch 42 is a switch that is operated for cursor movement in the case of performing operations of various menus that are graphically displayed and measurements, and is constituted approximately the same as the joystick 41. The freeze switch 43 is a switch that relates to display on the LCD 5.

The store switch 44 is a switch that is used for storing a still image in the memory card when the still image is displayed by depressing the freeze switch 43. The measurement execution switch 45 is a switch that is used when running measurement software. The freeze switch 43, the store switch 44, and the measurement execution switch 45 are constituted by adopting depression-type switches that, for example, perform ON/OFF control by a depression operation.

The WIDE switch 46 and the TELE switch 47 are switches that are used when performing enlargement and reduction of the endoscope image, respectively. The endoscope image that is imaged by the insertion portion 20 is enlarged or reduced as needed by the video signal processing circuit 12. Control of the magnification of this enlargement or reduction is performed by operation of the WIDE switch 46 and the TELE switch 47.

Figure 5:
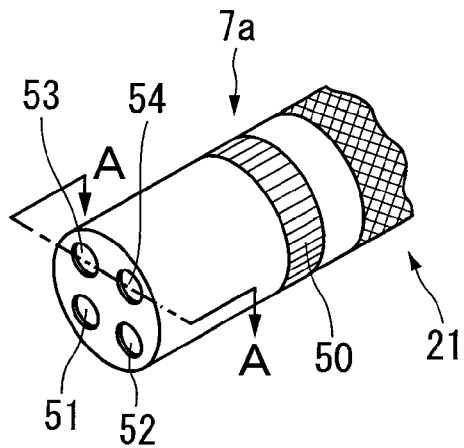
FIG. 5 is a perspective view of a stereo optical adapter that is used in the endoscope apparatus according to the embodiment of the present invention.
Figure 6:
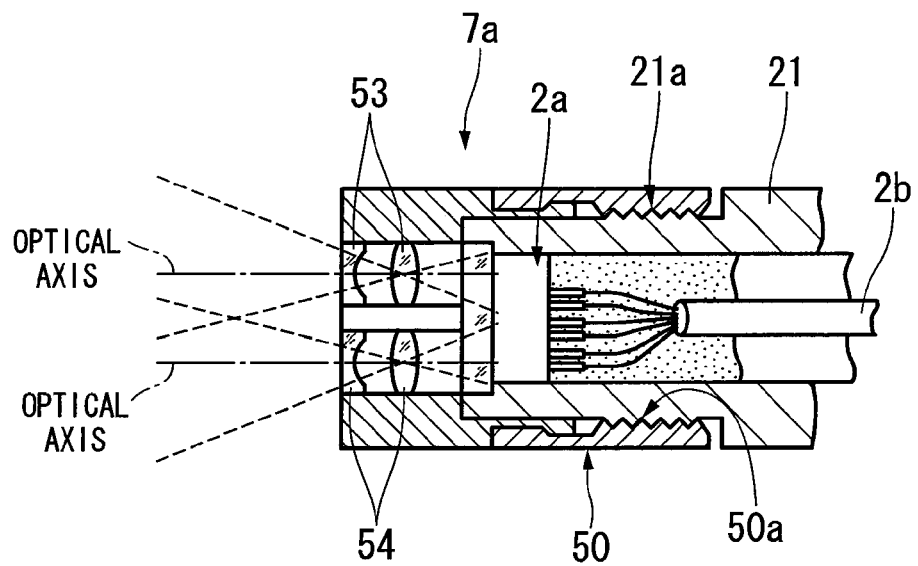
FIG. 6 is a cross-sectional view illustrating the internal configuration of the stereo optical adapter that is used in the endoscope apparatus according to the embodiment of the present invention.

FIGS. 5 and 6 show example configurations of the stereo optical adaptor 7a that is one of optical adaptors used in the endoscope apparatus 1 of the present embodiment. As shown in FIGS. 5 and 6, a pair of illumination lenses 51 and 52 and two object lens systems 53 and 54 are provided at the distal surface of the direct-view stereo optical adaptor 7a. As shown in FIG. 6, the optical adaptor 7a is integrally fixed to the distal portion 21 by screwing a male screw 50a of a fixing ring 50 with a female screw 21a formed in the distal portion 21.

As shown in FIG. 6, two optical images are formed via the two object lens systems 53 and 54 on an imaging surface of the solid-state imaging device 2a provided in the distal portion 21. Then, an image signal that has been subjected to photoelectric conversion by the solid-state imaging device 2a is supplied to the CCU 9 via a signal wire 2b and the endoscope unit 8 that are electrically connected to the CCU 9, is converted into a video signal, and thereafter is supplied to the video signal processing circuit 12.

Figure 7:
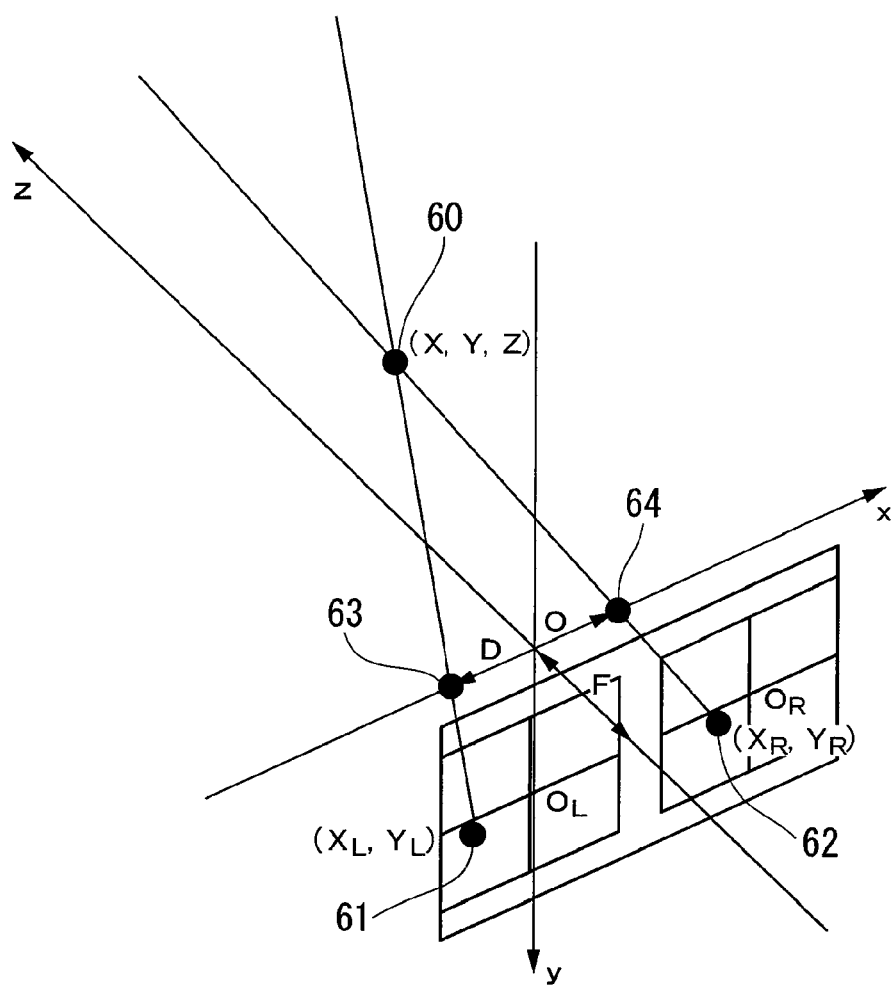
FIG. 7 is a reference view for explaining the method of calculating three-dimensional coordinates of a measurement point using the stereo measurement according to the embodiment of the present invention.

Next, the way of calculating three-dimensional coordinates of a measuring point by the stereo measurement will be described with reference to FIG. 7. For images that are captured by the left side and right side optical systems, three-dimensional coordinates (X, Y, Z) of a measurement target point 60 are calculated by the triangulation method using the following Equations (1) to (3). Note that it is assumed that the coordinates of a measuring point 61 and a corresponding point 62 on the left and right images that have been subjected to distortion correction are $(X_L, Y_L)$ and $(X_R, Y_R)$, respectively, the distance between optical centers 63 and 64 on the left side and right side is D, the focal length is F, and $t=D/(X_L-X_R)$.

$$X = t \times X_R + D/2 \quad (1)$$

$$Y = t \times Y_R \quad (2)$$

$$Z = t \times F \quad (3)$$

When the coordinates of the measuring point 61 and the corresponding point 62 are determined in the aforementioned manner, the three-dimensional coordinates of the measurement target point 60 are found using the parameters D and F. By calculating three-dimensional coordinates of a number of points, various measurements such as a point-to-point distance, the distance between a line connecting two points and one point, surface area, depth, and surface shape, are possible. In addition, it is possible to calculate a distance (object distance) from the left-side optical center 63 or the right-side optical center 64 to the subject. In order to carry out the aforementioned stereo measurement, optical data that shows the characteristics of the optical system including the distal portion 21 and the stereo optical adaptor are required. Details of the optical data are disclosed, for example, in Japanese Unexamined Patent Application, First Publication No. 2004-49638, so an explanation thereof will be omitted here.

Figure 8A:
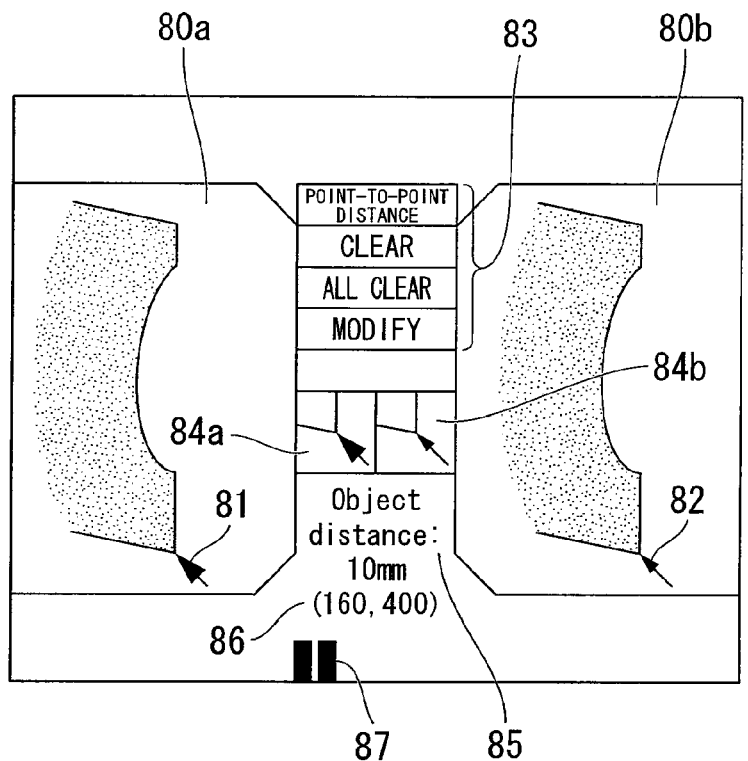
FIGS. 8A and 8B are reference views illustrating a measurement screen according to the embodiment of the present invention.

Next, the transition of a display screen (measurement screen) at the time of measurement mode will be described with reference to FIGS. 8A to 11. Hereinafter, the description is made using the point-to-point measurement by way of example. FIG. 8A shows a display screen at the start time of the measurement mode. A left image 80a and a right image 80b, which correspond to left and right subject images relating to the same subject as a measurement target captured by the stereo optical adapter, are displayed on the measurement screen. Further, a cursor 81 is displayed on the left image 80a, and a corresponding point cursor 82 is displayed on the right image 80b. The cursor 81 is for indicating a position of a measurement point. The corresponding point cursor 82 is for indicating a position of a corresponding point corresponding to the position of the cursor 81 on the left image 80a.

Various menus 83, zoom windows 84a and 84b, an object distance 85, and cursor coordinates 86 are displayed between the left image 80a and the right image 80b. These are displayed in a region of an image based on the image data excluding regions where the images of the subject as a measurement target (i.e., the left image 80a and the right image 80b) are displayed. This region corresponds to a region of an image of a mask which is built in the stereo optical adaptor and shields an incident light. An enlarged image in a surrounding region of the cursor 81 is displayed in the zoom window 84a, and an enlarged image in a surrounding region of the corresponding point cursor 82 is displayed in the zoom window 84b. The object distance 85 shows a measuring result of an object distance. The cursor coordinates 86 show image coordinates (i.e., two-dimensional coordinates) of the cursor 81.

An object distance indicator 87 is displayed in the lower portion of the measurement screen. The object distance indicator 87 is a scale which visually represents the object distance. The display configuration of the object distance indicator 87 varies in accordance with the object distance. Specifically, the number of square marks of the object distance indicator 87 increases as the object distance becomes longer. The color of the square marks in the object distance indicator 87 is set in accordance with the object distance. The color of texts of the object distance 85, the color of the cursor 81, and the color of the corresponding point cursor 82 can be also set in accordance with the object distance.

As described above, the user can move the cursor 81 by inputting a movement instruction of the cursor 81 through the remote controller 4. Along with the movement of the cursor 81, the corresponding point mark 82 is moved and the images in the zoom windows 84a and 84b are updated.

Figure 8B:
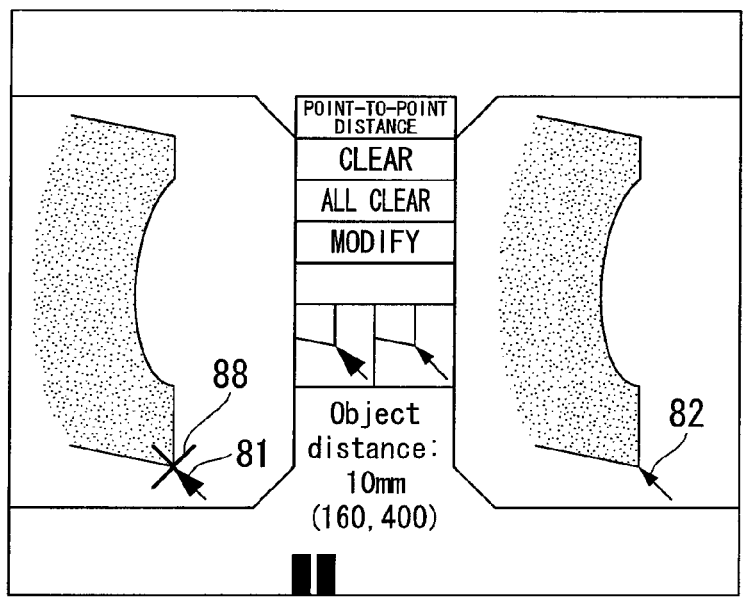

As shown in FIG. 8B, when the user inputs an instruction of designating (fixing) a measurement point after moving the cursor 81 to a desired position, a measurement point mark 88, which serves as a mark indicating the position of the designated measurement point, is displayed at the position of the cursor 81 (i.e., the position of the measurement point). After this moment, another measurement point mark which is different from the measurement point mark 88 is displayed on the measurement screen, and is moved on the measurement screen from the position of the cursor 81 toward the position of the corresponding point mark 82 (i.e., the position of the corresponding point).

Figure 9A:
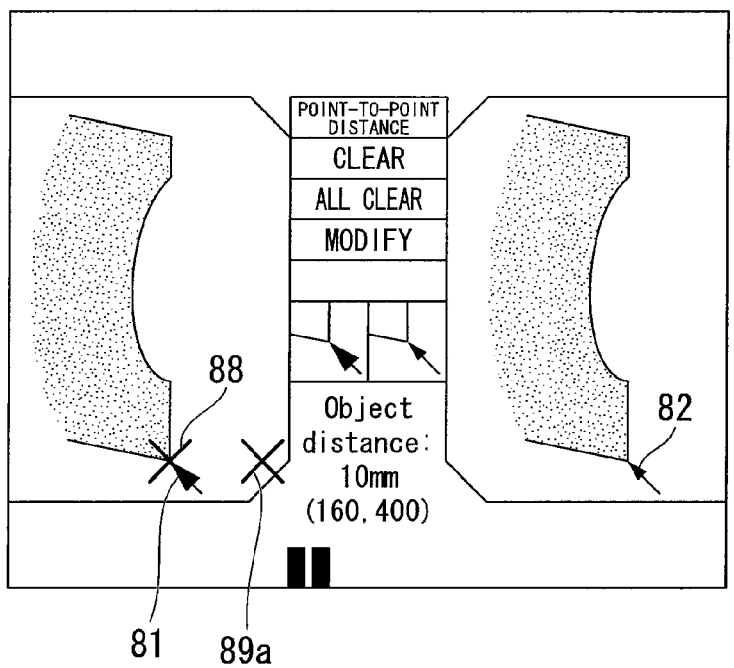
FIGS. 9A and 9B are reference views illustrating a measurement screen according to the embodiment of the present invention.
Figure 9B:
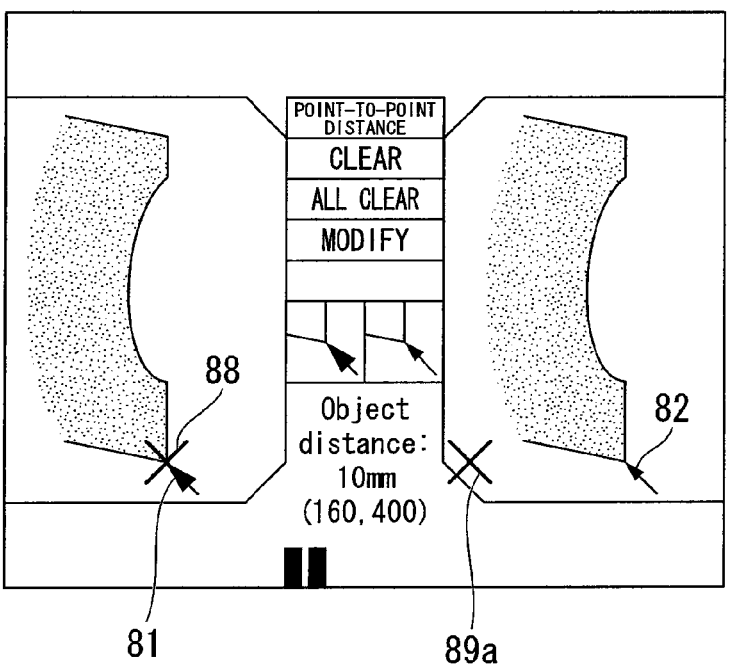

FIG. 9A shows a measurement screen at a point in time during a period when a measurement point mark 89a is moving from the position of the cursor 81 toward the position of the corresponding point cursor 82. FIG. 9B shows a measurement screen at another point in time during the period after the point in time of FIG. 9A. The measurement point mark 89a shown in FIG. 9B comes closer to the corresponding point cursor 82 than that shown in FIG. 9A.

Figure 10A:
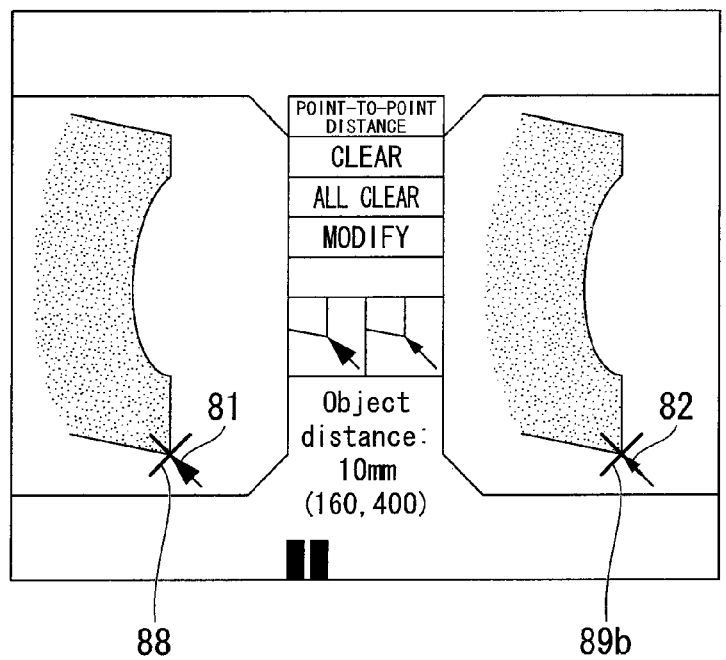
FIGS. 10A and 10B are reference views illustrating a measurement screen according to the embodiment of the present invention.

FIG. 10A shows a measurement screen at a point in time when the measurement point mark 89a reaches the position of the corresponding point cursor 82. The movement of the measurement point mark 89a is stopped when the measurement point mark 89a has reached the position of the corresponding point cursor 82, and functions as a corresponding point mark 89b which serves as a mark indicating the position of the corresponding point 82. When the measurement point mark 89a is moving on the measurement screen in this manner, it is expected to obtain an effect of attracting the user's eye to the measurement point mark 89a. When the measurement point mark 89a is moving from the position of the cursor 81, i.e., the position of the designated measurement point, to the position of the corresponding point cursor 82, the user's eye is also moving from the position of the measurement point to the position of the corresponding point. With this movement, it is possible to prompt the user to confirm the corresponding point. In the present embodiment, the movement of the measurement point mark 89a is controlled so that the movement time from the start of movement of the measurement point mark 89a to the completion of movement is constant (for example, one second), by way of example.

Figure 10B:
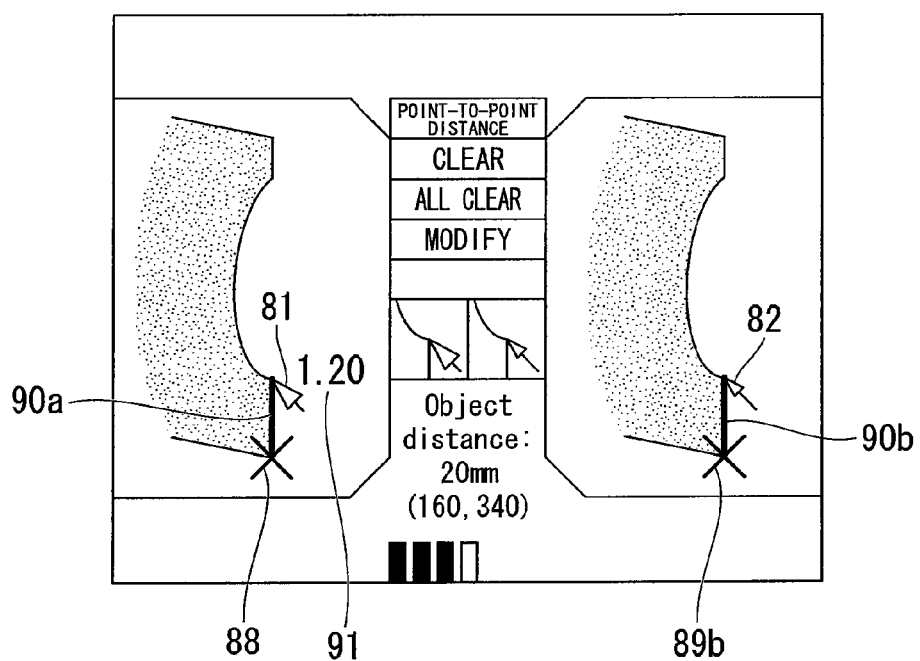

When a first measurement point has been designated in the manner described above, designation of a second measurement point is performed. FIG. 10B shows a measurement screen at a point in time during a period when the user is moving the cursor 81 in order to designate a second measurement point. In the present embodiment, the point-to-point distance between the three-dimensional coordinates of the first measurement point and the three-dimensional coordinates of the position of the cursor 81 is measured in real time. In the real time measurement, a measurement line 90a which connects the position of the cursor 81 and the position of the measurement point mark 88 to each other is displayed. In addition, a measurement line 90b which connects the position of the corresponding point cursor 82 and the position of the corresponding point mark 89b to each other is displayed. A measurement result 91 is also displayed showing the point-to-point distance between the three-dimensional coordinates based on the position of the cursor 81 and the position of the corresponding point cursor 82 and the three-dimensional coordinates based on the position of the measurement point mark 88 and the position of the corresponding point mark 89b. The measurement result 91 is updated in real time along with the movement of the cursor 81.

When the user inputs an instruction of designating (fixing) a second measurement point after moving the cursor 81 to a desired position, a measurement point mark, which serves as a mark indicating the position of the designated second measurement point, is displayed on the measurement screen in a similar manner to the designation of the first measurement point. Then, another measurement point mark which is different from this measurement point mark is moved on the measurement screen from the position of the cursor 81 toward the position of the corresponding point mark 82. At this time, the measurement result 91 can be moved together with the measurement point mark. With this movement, it is possible to prompt the user to confirm a second corresponding point.

Figure 11:
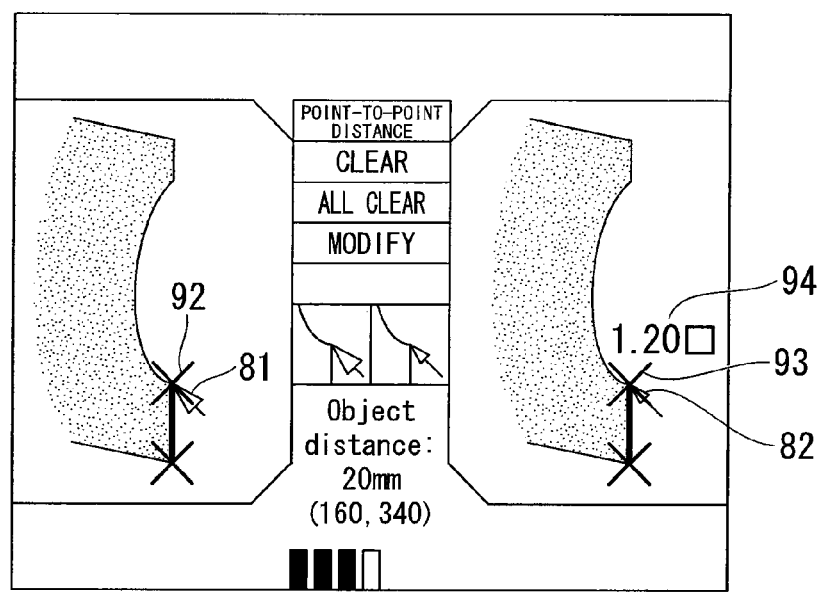
FIG. 11 is a reference view illustrating a measurement screen according to the embodiment of the present invention.

FIG. 11 shows a measurement screen at a point in time when the movement of the measurement point mark has been completed. A measurement point mark 92 is displayed at the position of the second measurement point (i.e., the position of the cursor 81), and a corresponding point mark 93 is displayed at the position of the second corresponding point (i.e., the position of the corresponding point cursor 82). The corresponding point mark 93 is the same as the measurement point mark after the completion of movement from the position of the measurement point. Further, the measurement result 91 after the completion of movement from the position of the measurement point is displayed as a measurement result tag 94.

Next, an operation of the endoscope apparatus 1 at the time of the measurement mode will be described. Hereinafter, the description is made using the point-to-point measurement by way of example. A first operation example will be described with reference to FIG. 12. When the measurement mode is started, the control section 18e initializes a variable indicating the number of designated measurement points (step S100). Subsequently, the control section 18e determines the type of instruction (the content of event) based on a signal from the remote controller 4 (step S105).

When the type of instruction shows the movement instruction of the cursor, the cursor position calculation section 18a calculates a movement amount of the cursor based on the signal from the remote controller 4. Then, the cursor position calculation section 18a calculates a position of the cursor at the next time (i.e., the position of the measurement point) by adding the calculated movement amount to the position of the cursor at the current time (step S110). Subsequently, the corresponding point calculation section 18b performs the matching processing to calculate a position, on the right image, of a corresponding point corresponding to the position of the cursor calculated in step S110 (step S115). Subsequently, the measurement section 18d calculates three-dimensional coordinates of a measurement target point based on the position of the cursor calculated in step S110 and the position of the corresponding point calculated in step S115 (step S120).

Subsequently, the display processing section 18c generates a graphic image signal of a cursor with its color set in accordance with the object distance (i.e., the z-coordinate of the measurement target point), and outputs it to the video signal processing circuit 12. At this time, the display processing section 18c controls the display position of the cursor so that the cursor is displayed at the cursor position calculated in step S110. As a result, the cursor is displayed on the measurement screen (step S125). In addition, the display processing section 18c generates a graphic image signal of a corresponding point mark and an object distance with their colors set in accordance with the object distance, respectively, and outputs it to the video signal processing circuit 12. At this time, the display processing section 18c controls the display position of the corresponding point mark so that the corresponding point mark is displayed at the position of the corresponding point calculated in step S115. As a result, the corresponding point mark and the object distance are displayed on the measurement screen (step S130).

Subsequently, the control section 18e determines a value of the variable indicating the number of designated measurement points (step S135). When the value of the variable is "0", the processing returns to step S105. When the value of the variable is "1", the display processing section 18c generates a graphic image signal of a measurement line with its color set in accordance with the object distance, and outputs it to the video signal processing circuit 12. As a result, the measurement line which connects the first measurement point mark and the cursor to each other is displayed on the measurement screen (step S140).

Subsequently, the measurement section 18d calculates a spatial distance, i.e., a point-to-point distance, between the three-dimensional coordinates of the first measurement point calculated in step S120 and the three-dimensional coordinates of the measurement point, which is indicated by the current cursor position, calculated in step S120 (step S145).

Subsequently, the display processing section 18c generates a graphic image signal of a measurement result with its color set in accordance with the object distance, and outputs it to the video signal processing circuit 12. As a result, the measurement result (real-time measurement result) of the point-to-point distance is displayed on the measurement screen (step S150). Then, the processing returns to step S105.

On the other hand, when the type of instruction shows the designation instruction of a measurement point in step S105, the cursor position calculation section 18a designates (recognizes) the position of the cursor which is lastly calculated in step S110 as a position of a measurement point of the measurement target (step S155). Subsequently, the display processing section 18c generates a graphic image signal of two measurement point marks with their colors set in accordance with the object distance, and outputs it to the video signal processing circuit 12. At this time, the display processing section 18c controls the display position of the measurement point marks so that the measurement point mark is displayed at the position of the measurement point designated in step S155. As a result, the two measurement point marks are displayed on the measurement screen in a state where the two measurement point marks overlap each other (step S160). Subsequently, the control section 18e determines a value of the variable indicating the number of designated measurement points (step S165).

When the value of the variable is "0", the display processing section 18c performs a control of deleting (hiding) one of the two measurement point marks displayed at the position of the measurement point designated in step S155. Further, the display processing section 18c performs a control of displaying a measurement point mark, which is the same as the deleted measurement point mark, at a position different from the positions of the measurement point designated in step S155 and the corresponding point corresponding to this measurement point. In order to make the measurement point mark seem to be moving from the position of the measurement point to the corresponding point when the user looks, the measurement point mark is firstly displayed at a position which is in the vicinity of the position of the measurement point and is slightly shifted from the position of the measurement point toward the corresponding point.

Next, the display processing section 18c performs a control of deleting the displayed measurement point mark which is slightly shifted toward the corresponding point, and of displaying the deleted measurement point mark at a position which is slightly shifted from the display position before deleting toward the corresponding point. By repeating this procedure, the measurement point mark is moving on the measurement screen from the position of the measurement point to the position of the corresponding point. Then, at an appropriate point in time, the display processing section 18c performs a control of deleting the displayed measurement point mark which is shifted toward the corresponding point, and of displaying the deleted measurement point mark at the position of the corresponding point. When the measurement point mark is displayed at the position of the corresponding point, the display processing section 18c completes the movement of the measurement point mark (step S170). Subsequently, the control portion 18e sets the value of the variable indicating the number of designated measurement points to "1" (step S175). Subsequently, the processing returns to step S105.

On the other hand, when the value of the variable indicating the number of designated measurement points is "1" in step S165, the display processing section 18c performs a control of moving the measurement result and one of the two measurement point marks, which are displayed at the position of the measurement point designated in step S155, from the position of the measurement point designated in step S155 to the position of the corresponding point corresponding to this measurement point (step S180). The control contents in step S180 are similar to the control contents in step S170.

Subsequently, the display processing section 18c performs a control of deleting the movement result which has been moved in step S180 (step S185). Further, the display processing section 18c generates a graphic image signal of a measurement result tag with its color set in accordance with the object distance, and outputs it to the video signal processing circuit 12. As a result, the measurement result tag is displayed on the measurement screen (step S190). Subsequently, the control section 18e sets the value of the variable indicating the number of designated measurement points to "0" (step S195). Subsequently, the processing returns to step S105.

Figure 12:
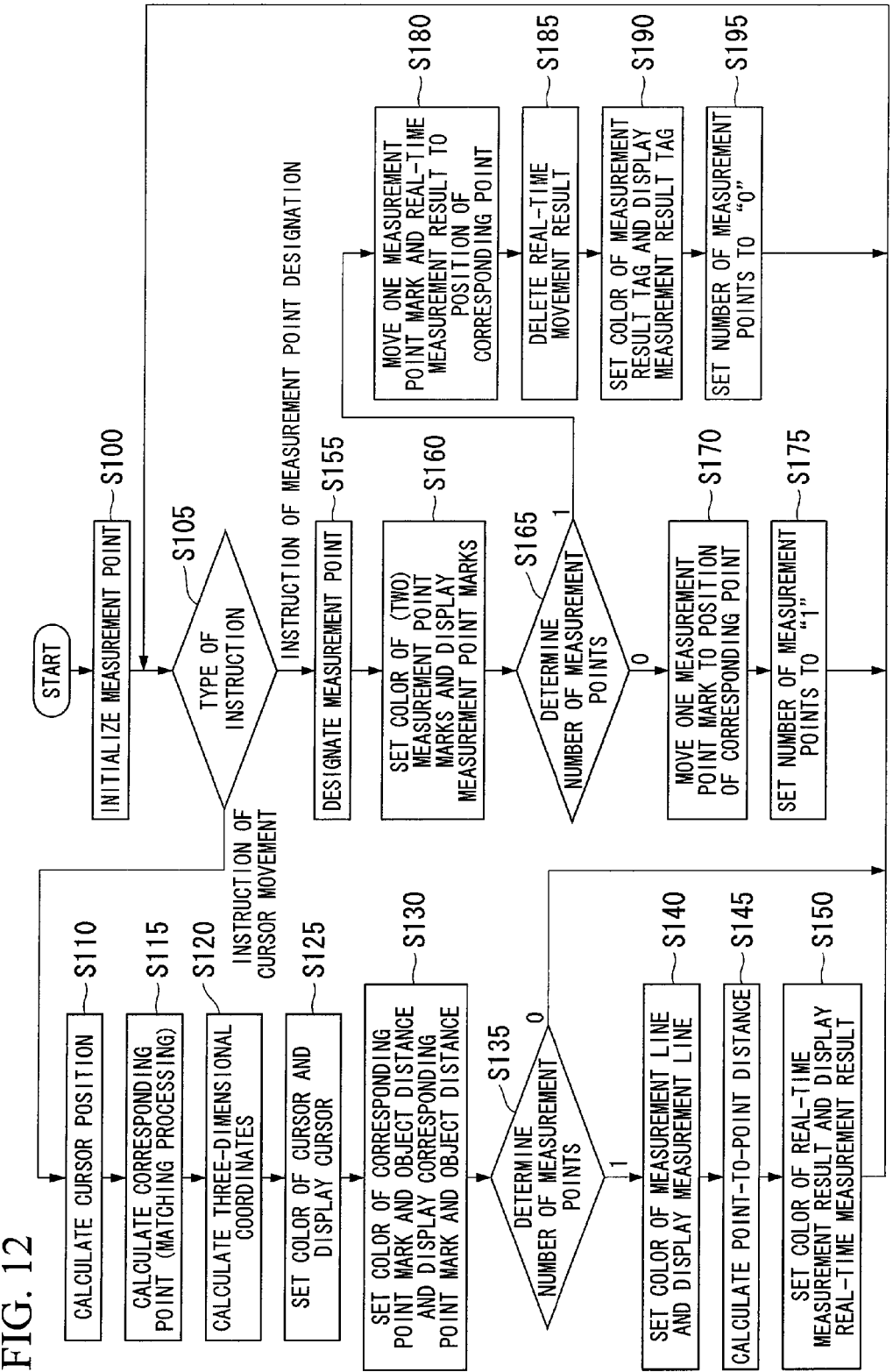
FIG. 12 is a flow chart illustrating the procedure at the time of a measurement mode according to the embodiment of the present invention.

As shown in FIG. 12, subsequent processings will not be performed until the movement of the measurement point mark in step 170 or the movement of the measurement point mark and the measurement result in step S180 is completed. Therefore, during a period when the measurement point mark is moving, since the control section 18e voids the movement instruction of the cursor and the designation instruction of a measurement point, the user cannot move the cursor and designate a measurement point. This means that the movement of the cursor and the designation of a measurement point are prohibited during the period when the measurement point mark is moving. Accordingly, it is possible to more reliably prompt the user to confirm the corresponding point.

Next, a second operation example will be described with reference to FIGS. 13 and 14. In the second operation example, after the user inputting the designation instruction of a measurement point and completing the movement of the measurement point mark from the position of the measurement point to the position of the corresponding point, processing of making the user demonstratively confirm the corresponding point is performed. The procedure shown in FIG. 13 is different from the procedure shown in FIG. 12 in that processing of making the user demonstratively confirm the corresponding point (step S200) is added between step S170 and step S175, and between step S190 and step S195.

Figure 14:
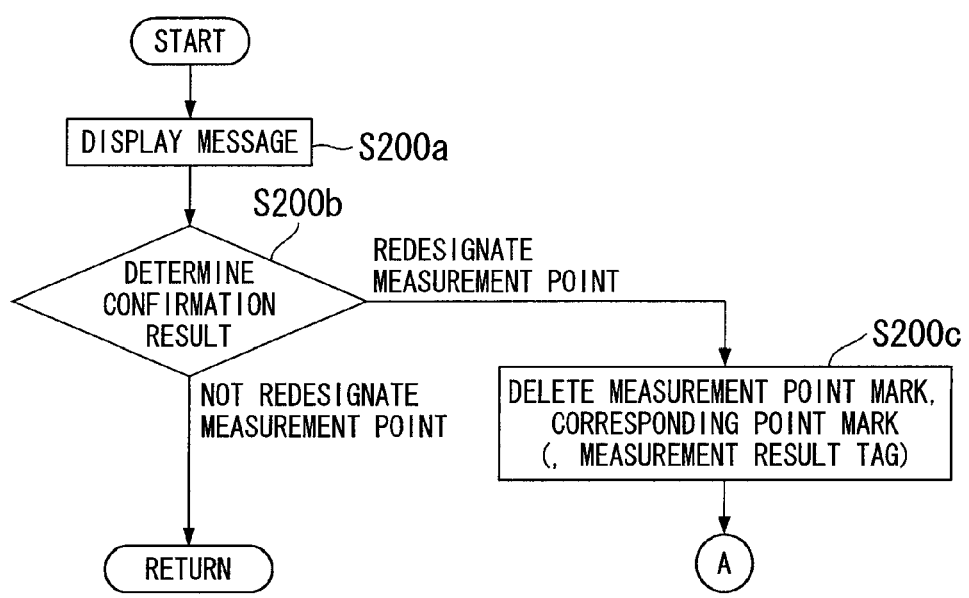
FIG. 14 is a flow chart illustrating the procedure at the time of the measurement mode according to the embodiment of the present invention.

FIG. 14 shows processing in step S200. First, the display processing section 18c generates a graphic image signal including a message for prompting the user to confirm the corresponding point, and outputs it to the video signal processing circuit 12. As a result, the message is displayed on the measurement screen (step S200a). Subsequently, the control section 18e determines the type of instruction based on a signal from the remote controller 4 (step S200b).

After the message is displayed, the user is required of determining whether or not to redesignate a measurement point based on the confirmation result of the corresponding point, and of inputting the determination result. When the type of instruction shows that the redesignation of a measurement point is not necessary, the processing returns to step S105. In this case, it is speculated that the user determines that the corresponding point is good. On the other hand, when the type of instruction shows that the redesignation of a measurement point is necessary, the display processing section 18c performs a control of deleting the measurement point mark and the corresponding point mark (in the case of step S200 after step S190, also the measurement result tag) on the display screen (step S200c). In this case, it is speculated that the user determines that the corresponding point is not good. Subsequently, the processing proceeds to step S175 or step S195.

Figure 13:
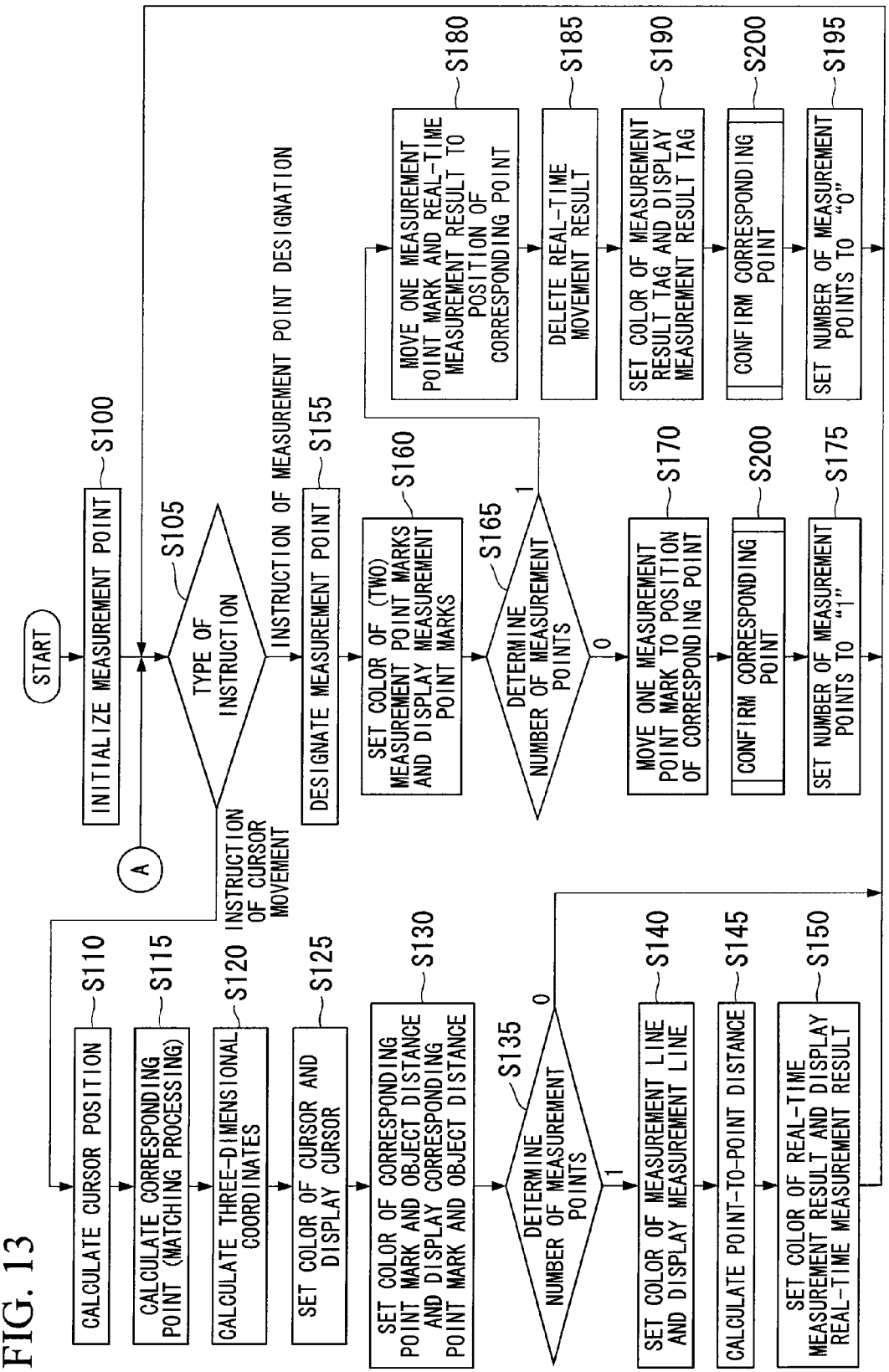
FIG. 13 is a flow chart illustrating the procedure at the time of the measurement mode according to the embodiment of the present invention.

As shown in FIGS. 13 and 14, subsequent processings will not be performed until the confirmation result of the corresponding point is input. Therefore, until the confirmation result of the corresponding point is input, since the control section 18e voids the movement instruction of the cursor and the designation instruction of a measurement point, the user cannot move the cursor and designate a measurement point. This means that the movement of the cursor and the designation of a measurement point are prohibited until the confirmation result of the corresponding point is input. Accordingly, it is possible to more reliably prompt the user to confirm the corresponding point.

Although the user always inputs any confirmation result in the above description, the user may input the confirmation result only when redesignating a measurement point. For example, the processing may proceed to step S200c when an instruction of redesignating a measurement point is input within a predetermined period from the display of the message, and the processing may proceed to step S175 or step S195 when an instruction of redesignating a measurement point is not input within the predetermined period from the display of the message.

Figure 15A:
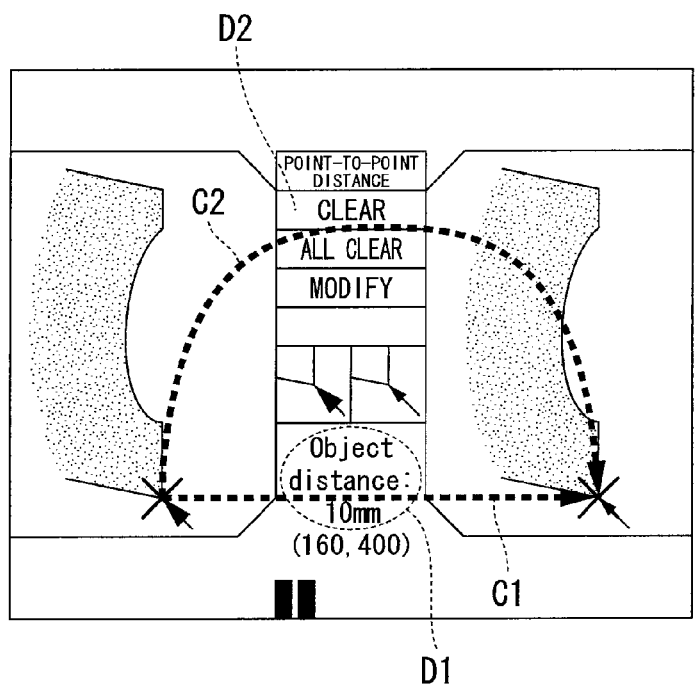
FIGS. 15A and 15B are reference views illustrating a measurement screen according to the embodiment of the present invention.

Next, the movement of the measurement point mark is additionally explained. The measurement point mark may move in a straight line from the position of the measurement point toward the position of the corresponding point. Alternatively, the measurement point mark may move in a curve or move in a zigzag manner. For example, both of a pathway C1 and a pathway C2 shown in FIG. 15A are employable as a pathway of the measurement point mark. The pathway C1 is the shortest path from the position of the measurement point to the position of the corresponding point. In the case of the pathway C1, the measurement point mark passes through a region D1, on which the above-described image of the mask is displayed, in the middle of the pathway C1. In the case of the pathway C2, the measurement point mark passes through a region D2, on which the graphic images are displayed so as to be superimposed on the image of the mask, in the middle of the pathway C2.

Figure 15B:
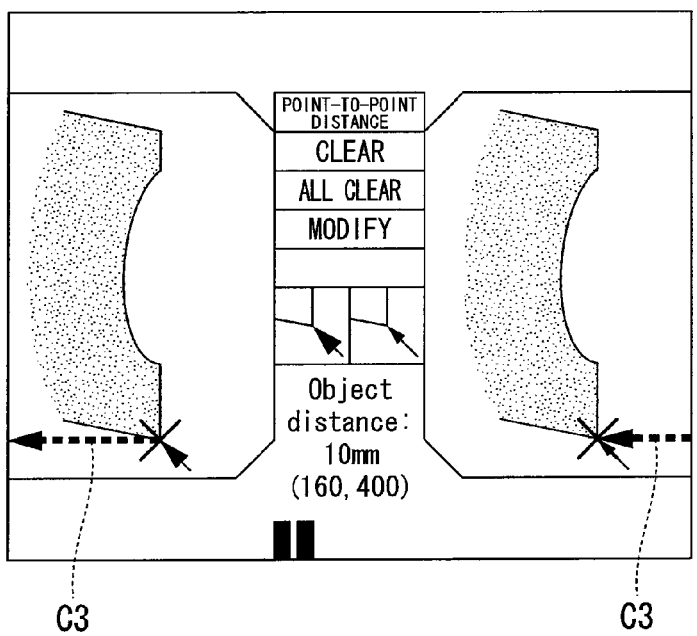

The measurement point mark may be moved via a pathway C3 shown in FIG. 15B. However, in this case, there is a possibility that the user may be confused since the measurement point mark passingly disappears from the measurement screen in the middle of the pathway C3. Therefore, the pathway C1 and the pathway C2 are more preferable than the pathway C3. In the case of desiring to shorten a pathway of the measurement point mark is as much as possible, it is preferable that for all points on the pathway, the distance from each of the points to the measurement point is shorter than the distance from the measurement point to the corresponding point, and the distance from each of the points to the corresponding point is shorter than the distance from the measurement point to the corresponding point.

Figure 16A:
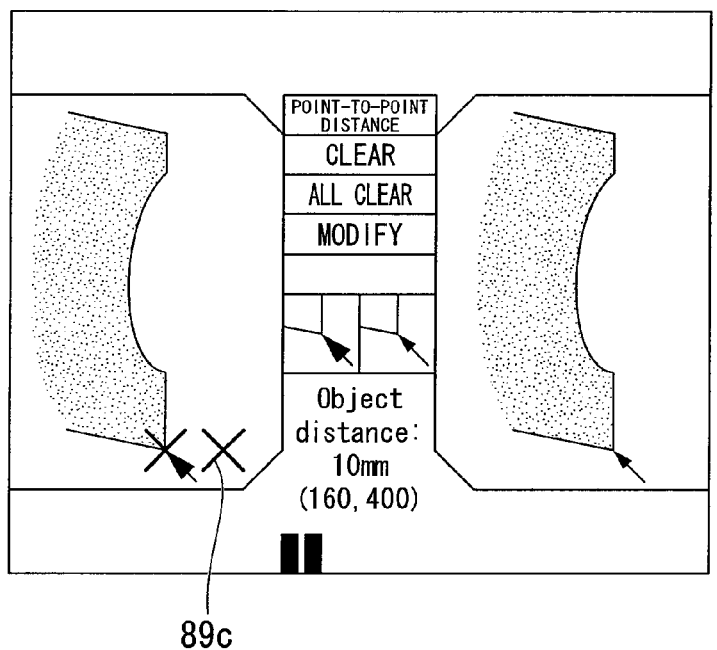
FIGS. 16A and 16B are reference views illustrating a measurement screen according to the embodiment of the present invention.
Figure 16B:
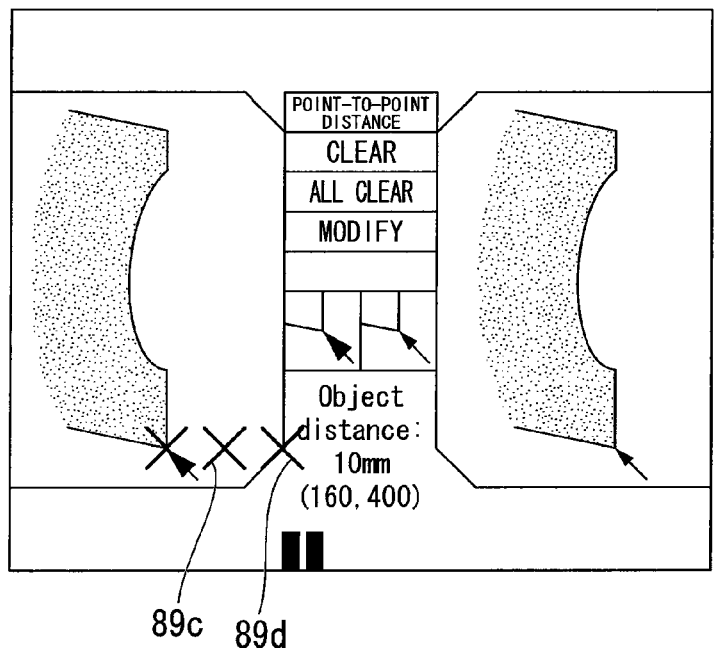

Further, instead of moving the measurement point mark, new measurement point marks may be sequentially displayed from the position of the measurement point toward the position of the corresponding point. For example, as shown in FIG. 16A, when the designation instruction of a measurement point is input, the display processing section 18c performs a control of displaying a new measurement point mark 89c at a position which is shifted from the position of the measurement point toward the corresponding point. Next, as shown in FIG. 16B, the display processing section 18c performs a control of displaying a new measurement point mark 89d at a position which is shifted from the position of the measurement point mark 89c toward the corresponding point. This procedure is repeated until a new measurement point mark is displayed at the position of the corresponding point. When the new measurement point mark is displayed at the position of the corresponding point, the new displayed measurement point marks other than the measurement point marks displayed at the corresponding point and the measurement point are deleted. Note that the measurement point mark displayed at the corresponding point functions as a corresponding point mark.

Figure 17A:
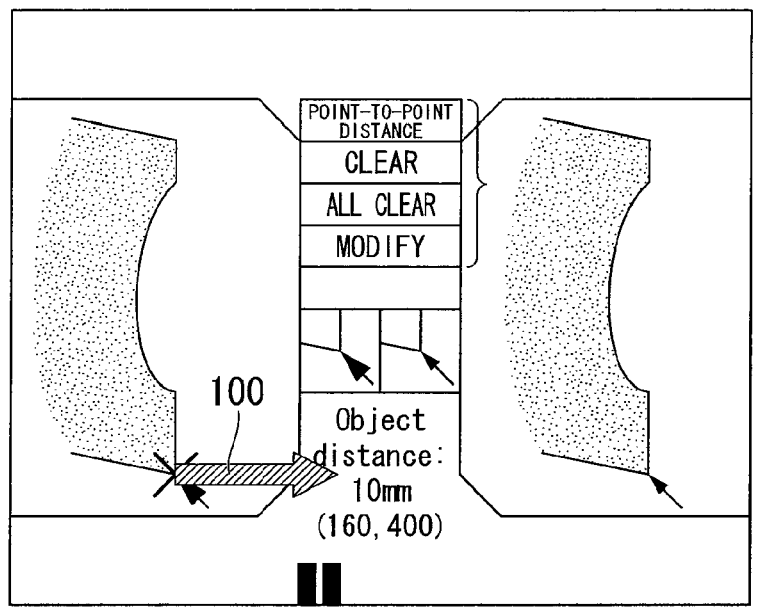
FIGS. 17A and 17B are reference views illustrating a measurement screen according to the embodiment of the present invention.
Figure 17B:
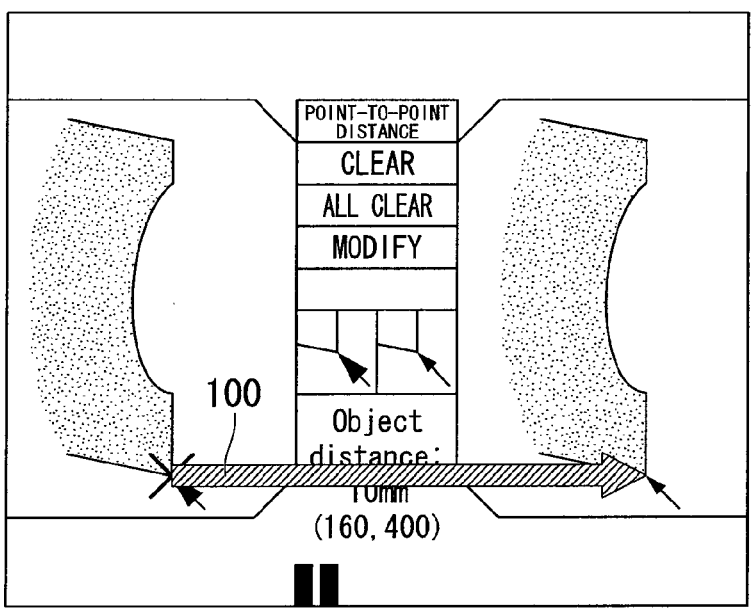

Alternatively, an arrow and the like that is extending from the position of the measurement point toward the position of the corresponding point may be displayed. For example, when the designation instruction of a measurement point is input, the display processing section 18c performs a control of displaying a measurement point mark at the position of the measurement point, and performs a control of displaying an arrow which connects to each other the position of the measurement point and a position which is shifted from the position of the measurement point toward the corresponding point by a distance d1. Next, the display processing section 18c performs a control of deleting the arrow displayed at the previous point in time, and of displaying a new arrow which connects to each other the position of the measurement point and a position which is shifted from the position of the measurement point toward the corresponding point by a distance d2 (d1<d2). This procedure is repeated until an arrow which connects the position of the measurement point and the position of the corresponding point to each other is displayed. FIG. 17A shows a measurement screen at a point in time after the designation instruction of a measurement point is input. An arrow 100 which begins at the position of the measurement point is displayed. FIG. 17B shows a measurement screen at a point in time when the arrow 100 reaches the position of the corresponding point. Immediately after this time, the arrow 100 is deleted and a corresponding point mark is displayed at the position of the corresponding point.

The measurement point mark may be emphasized and displayed immediately after the measurement point mark has been moved to the position of the corresponding point. For example, within a predetermined period after the completion of movement, the measurement point mark may be blinked, be enlarged, or be displayed while it changes its size periodically. Of course, the moving measurement point mark may be emphasized and displayed.

Figure 18A:
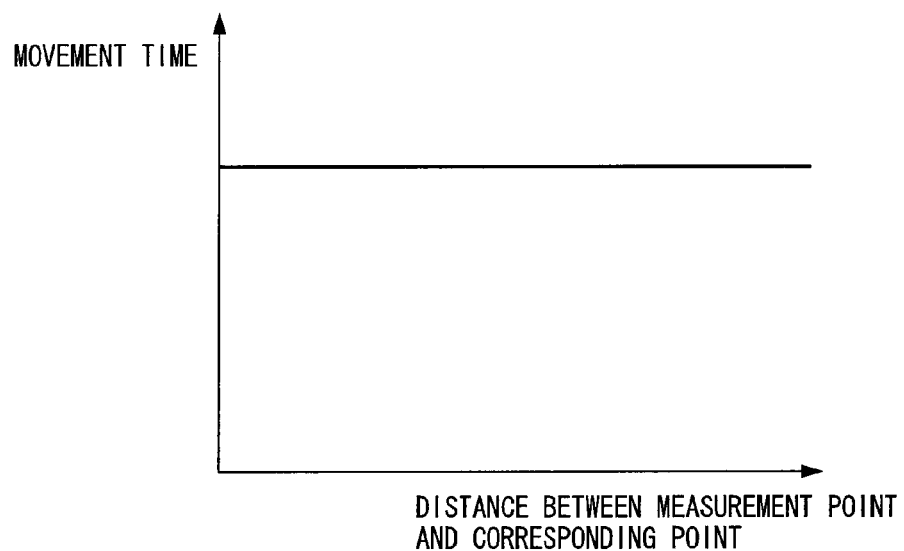
FIGS. 18A and 18B are reference views illustrating the movement time of a measurement point mark according to the embodiment of the present invention.

The movement speed or the movement time of the measurement point mark may be varied. FIG. 18A shows the movement time elapsing from the start of movement of the measurement point mark until the measurement point mark reaching the corresponding point in the case where the designation instruction of a measurement point is input, in accordance with the distance between the measurement point and the corresponding point. The present embodiment describes the case where the movement time is constant regardless of the distance between the measurement point and the corresponding point, by way of example. Therefore, the user visually feels that the movement speed of the measurement point mark is faster as the distance between the measurement point and the corresponding point is longer. Note that in the case where the movement speed is constant regardless of the distance between the measurement point and the corresponding point, when the distance between the measurement point and the corresponding point is short, the movement of the measurement point mark completes in an instant. Therefore, there is a possibility that the user cannot be aware of the movement of the measurement point mark. However, when the movement time is constant regardless of the distance between the measurement point and the corresponding point, it is possible for the user to reliably recognize the state that the measurement point mark is moving.

Figure 18B:
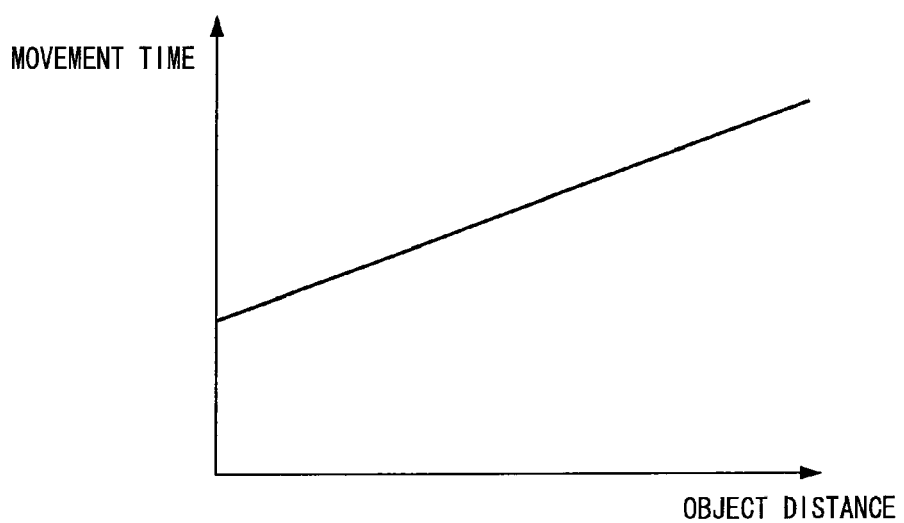

Alternatively, the movement speed or the movement time of the measurement point mark may be changed in accordance with the object distance. FIG. 18A shows the movement time elapsing from the start of movement of the measurement point mark until the measurement point mark reaching the corresponding point in the case where the designation instruction of a measurement point is input, in accordance with the object distance. FIG. 18B shows the case where the movement time becomes longer as the object distance is longer (i.e., the subject is further), by way of example. This enables the user to provide a visual effect in accordance with the object distance, and it is thereby possible to more reliably prompt the user to confirm the corresponding point.

Figure 19:
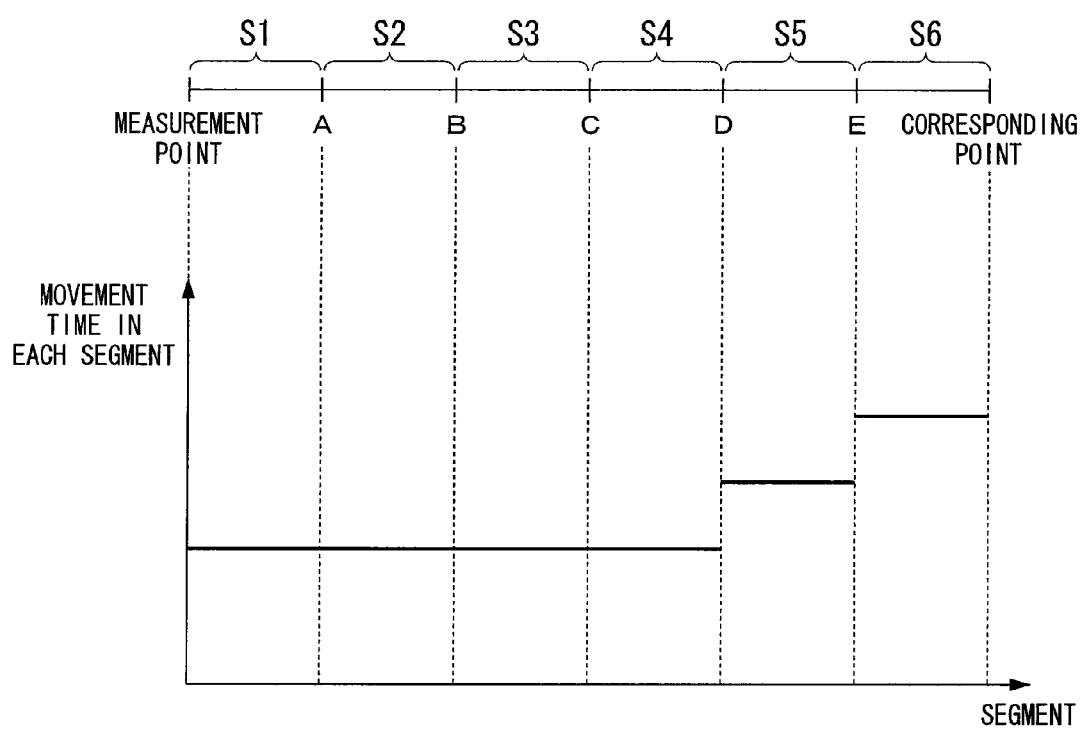
FIG. 19 is a reference view illustrating the method of controlling the measurement speed of the measurement point mark according to the embodiment of the present invention.
Figure 20A:
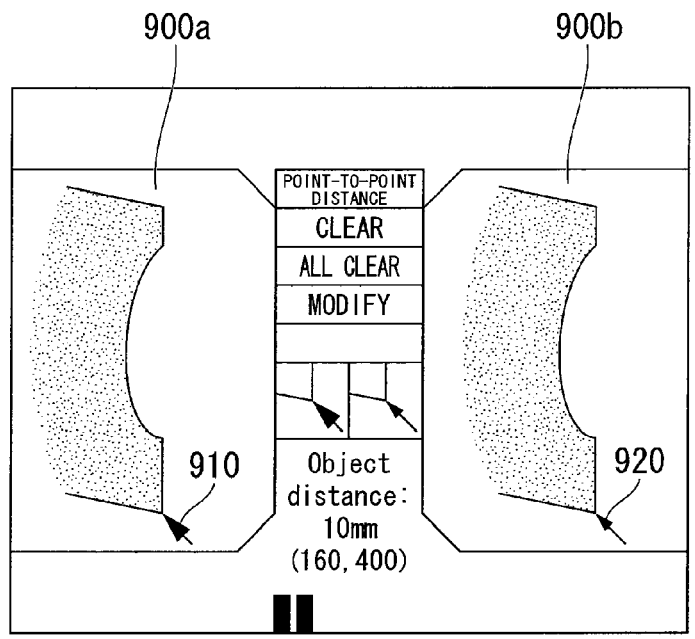
FIGS. 20A and 20B are reference views illustrating a conventional measurement screen.
Figure 20B:
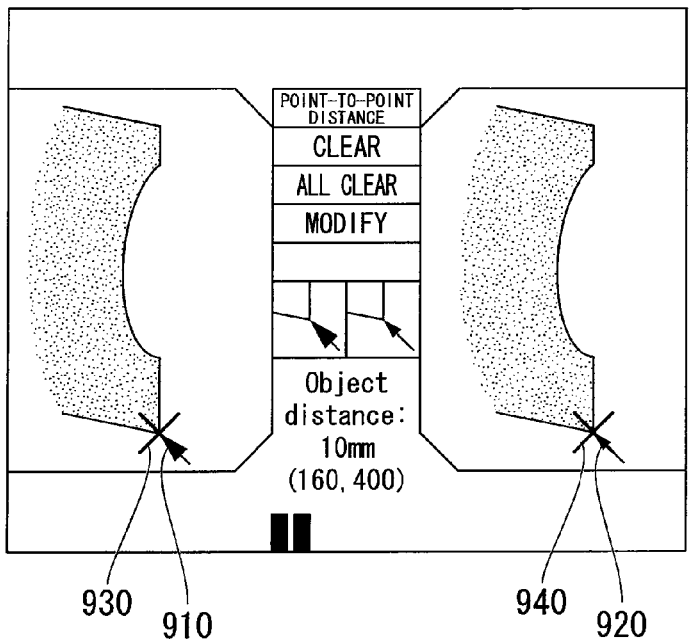

The movement speed may not be constant. For example, the movement of the measurement point mark may become slow when the measurement point mark approaches the position of the corresponding point. FIG. 19 shows an example of the way of controlling the movement speed of the measurement point mark. A pathway of movement of the measurement point mark from the measurement point to the corresponding point is divided into six segments S1 to S6, and boundary points of the segments are assumed to be points A to E, respectively. As shown in FIG. 19, the movement time is controlled for each segment.

In the example shown in FIG. 19, the movement time in each segment of the segments S1 to S4 is constant. On the other hand, the movement time in the segment S5 is longer than the movement time in each segment of the segments S1 to S4, and the movement time in the segment S6 is longer than the movement time in the segment S5. In other words, although the movement speed in each segment of the segments S1 to S4 is constant, the movement speed in the segment S5 is slower than the movement speed in each segment of the segments S1 to S4, and the movement speed in the segment S6 is slower than the movement speed in the segment S5. The movement time in each segment is controlled, for example, in accordance with the distance from the start point of each segment (i.e., the measurement point and the points A to E) to the measurement point or the corresponding point. By varying the movement of the measurement point mark in this manner, it is expected to obtain an effect of attracting the user's eye to the measurement point mark.

In the above description, the measurement point mark or the arrow is displayed as a mark for attracting the user's eye. However, other types of mark such as shape, text, sign, and the like may be used as long as it has a visible size and can function as a mark. In addition, as an auxiliary function, an audio which prompts the user to confirm the corresponding point may be generated from the speaker 35.

As described above, in the present embodiment, when the user designates a measurement point, the measurement point mark is displayed at the position of the measurement point, and then the measurement point mark is moved toward the position of the corresponding point. As a result, it is possible to prompt the user to move the user's eye from the position of the measurement point to the position of the corresponding point. Therefore, it is possible to prompt the user to confirm the corresponding point.

In addition, when prohibiting the designation of a next measurement point during a period from the designation of a measurement point to the completion of movement of the measurement point mark, it is possible to more reliably prompt the user to confirm the corresponding point. Further, when prohibiting the designation of a next measurement point during a period from the designation of a measurement point to the input of the confirmation result of the corresponding point by the user, it is possible to more reliably prompt the user to confirm the corresponding point.

When controlling the movement speed or the movement time of the measurement point mark in accordance with the object distance which is a criterion for measurement accuracy, it is possible to provide the user with a visual effect in accordance with the object distance. Therefore, it is possible to more reliably prompt the user to confirm the corresponding point. When controlling the movement speed or the movement time of the measurement point mark in accordance with the distance between the position of the measurement point and the position of the corresponding point, it is possible to ensure the user of an adequate time for recognizing the movement of the measurement point mark. Therefore, it is possible to more reliably prompt the user to confirm the corresponding point. When controlling the movement speed or the movement time of the measurement point mark in accordance with the distance between the position of the measurement point mark which is moving and the position of the measurement point or the position of the corresponding point, it is possible to provide the user with a visual effect in accordance with the change in movement of the measurement point mark. Therefore, it is possible to more reliably prompt the user to confirm the corresponding point.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

According to an aspect of the present invention, when a first position is designated, a mark is displayed at the first position, subsequently a mark is displayed at a third position, and subsequently a mark is displayed at a second position. As a result, it is possible to prompt the user to move the user's eye from the first position to the second position. Therefore, it is possible to prompt the user to confirm the corresponding point.

What is claimed is:

1. An endoscope apparatus, comprising:
   a display device that displays a first image and a second image, the first image and the second image being contained in image data of a subject captured by an imaging unit of the endoscope apparatus;
   a designation section that designates a first position on the first image in accordance with an instruction input through an input device;
   a position calculation section that calculates a second position on the second image, the second position corresponding to the first position on the first image;
   a display control section that, when the first position is designated, performs a control of displaying a first mark at the first position, subsequently displaying a third mark at a third position which is different from the first and second positions and which does not correspond to the first position on the first image or the second position on the second image, and subsequently displaying a second mark at the second position; and
   a measurement section that performs measurement relating to the subject based on the first and second positions,
   wherein the display control section performs a control of displaying the third mark such that the third mark moves from the first position to the second position while passing through the third position.

2. The endoscope apparatus according to claim 1, wherein a distance between the third position and the first position is shorter than a distance between the first position and the second position, and a distance between the third position and the second position is shorter than the distance between the first position and the second position.

3. The endoscope apparatus according to claim 1, wherein the third position is located in a region excluding a region which the subject occupies.

4. The endoscope apparatus according to claim 1, wherein the display control section prohibits a designation of a position on the first image during a period of time from the designation of the first position to the display of the second mark at the second position.

5. The endoscope apparatus according to claim 1, wherein the display control section prohibits a designation of a position on the first image during a period of time from the designation of the first position to the input of information which indicates that the second position has been confirmed through the input device.

6. The endoscope apparatus according to claim 1, wherein:
   the measurement section measures a distance to the subject based on the first position and the second position; and
   the display control section controls a movement speed or a movement time of the third mark based on the distance.

7. The endoscope apparatus according to claim 1, wherein the display control section controls the movement speed or the movement time of the third mark based on a distance between the first position and the second position.

8. The endoscope apparatus according to claim 1, wherein:
   the image data is stereo image data;
   the first image is a left image of the stereo image data; and
   the second image is a right image of the stereo image data.

9. The endoscope apparatus according to claim 1, wherein the display control section performs a control of displaying the marks at the first, second and third position with animation effect sequentially from the first position to the second position through the third position.

10. An endoscope apparatus, comprising:
    a display device that displays a first image and a second image, the first image and the second image being contained in image data of a subject captured by an imaging unit of the endoscope apparatus;
    a designation section that designates a first position on the first image in accordance with an instruction input through an input device;
    a position calculation section that calculates a second position on the second image, the second position corresponding to the first position on the first image;
    a display control section that, when the first position is designated, performs a control of displaying a first mark at the first position, subsequently displaying a third mark at a third position which is different from the first and second positions, and which does not correspond to the first position on the first image or the second position on the second image, and subsequently displaying a second mark at the second position; and
    a measurement section that performs measurement relating to the subject based on the first and second positions,
    wherein the display control section performs a control of displaying the third mark such that the third mark moves from the first position to the second position while passing through a plurality of the third positions, and controls a movement speed or a movement time of the third mark at a time of movement from the first position or the third position to the subsequent third position or the second position, based on a distance between a respective one of the plurality of the third positions and the first position or the second position.

11. An endoscope apparatus comprising:
a display device that displays a first image and a second image, the first image and the second image being contained in image data of a subject captured by an imaging unit of the endoscope apparatus;
a designation section that designates a first position on the first image in accordance with an instruction input through an input device;
a position calculation section that calculates a second position on the second image, the second position corresponding to the first position on the first image;
a display control section that, when the first position is designated, performs a control of displaying a first mark at the first position, subsequently displaying a third mark at a third position which is different from the first and second positions, and which does not correspond to the first position on the first image or the second position on the second image, and subsequently displaying a second mark at the second position; and
a measurement section that performs measurement relating to the subject based on the first and second positions,
wherein the display control section performs a control of displaying the third mark such that the third mark moves from the first position to the second position while passing through a plurality of the third positions.

12. An endoscope apparatus, comprising:
a display device that displays a first image and a second image, the first image and the second image being contained in image data of a subject captured by an imaging unit of an endoscope apparatus;
a designation section that designates a first position on the first image in accordance with an instruction input through an input device;
a position calculation section that calculates a second position on the second image, the second position corresponding to the first position on the first image;
a display control section that, when the first position is designated, performs a control of displaying a mark at the first position, subsequently displaying a mark at a third position which is different from the first and second positions, and subsequently displaying a mark at the second position; and
a measurement section that performs measurement relating to the subject based on the first and second positions;
wherein the display control section performs a control of displaying the marks at the first, second and third position with animation effect sequentially from the first position to the second position through the third position.

* * * * *